United States Patent [19]
Khosravi et al.

[11] Patent Number: 6,048,360
[45] Date of Patent: *Apr. 11, 2000

[54] METHODS OF MAKING AND USING COILED SHEET GRAFT FOR SINGLE AND BIFURCATED LUMENS

[75] Inventors: Farhad Khosravi, San Mateo; Michael Hogendijk, Palo Alto; John Spiridigliozzi, Belmont; Michael R. Ross, Hillsborough; Himanshu Patel, San Jose, all of Calif.

[73] Assignee: Endotex Interventional Systems, Inc., Menlo Park, Calif.

[*] Notice: This patent is subject to a terminal disclaimer.

[21] Appl. No.: 09/047,805

[22] Filed: Mar. 25, 1998

Related U.S. Application Data

[63] Continuation-in-part of application No. 08/820,213, Mar. 18, 1997, Pat. No. 5,824,054.

[51] Int. Cl.$^7$ .......................................................... A64F 2/06
[52] U.S. Cl. .................................... 623/1; 623/12; 600/36
[58] Field of Search ................................ 623/1, 12; 600/36

[56] References Cited

U.S. PATENT DOCUMENTS

| | | | |
|---|---|---|---|
| 4,577,631 | 3/1986 | Kreamer | 128/334 R |
| 4,665,918 | 5/1987 | Garza et al. | 128/343 |
| 5,078,726 | 1/1992 | Kreamer | 606/194 |
| 5,100,429 | 3/1992 | Sinofsky et al. | 606/195 |
| 5,211,658 | 5/1993 | Clouse | 623/1 |
| 5,219,355 | 6/1993 | Parodi et al. | 606/191 |
| 5,266,073 | 11/1993 | Wall | 623/1 |
| 5,275,622 | 1/1994 | Lazarus et al. | 623/1 |
| 5,330,500 | 7/1994 | Song | 606/198 |
| 5,366,473 | 11/1994 | Winston et al. | 606/198 |
| 5,423,885 | 6/1995 | Williams | 623/1 |
| 5,441,515 | 8/1995 | Khosravi et al. | 606/194 |
| 5,443,500 | 8/1995 | Sigwart | 623/1 |
| 5,456,713 | 10/1995 | Chuter | 623/1 |
| 5,571,173 | 11/1996 | Parodi | 623/1 |
| 5,575,817 | 11/1996 | Martin | 623/1 |
| 5,578,075 | 11/1996 | Dayton | 623/1 |
| 5,609,627 | 3/1997 | Goicoechea et al. | 623/1 |
| 5,618,299 | 4/1997 | Khosravi et al. | 623/1 |
| 5,632,840 | 5/1997 | Campbell . | |
| 5,649,977 | 7/1997 | Campbell | 623/1 |
| 5,700,286 | 12/1997 | Tartaglia et al. | 623/1 |
| 5,766,710 | 6/1998 | Turnlund et al. | 623/1 |
| 5,824,052 | 10/1998 | Khosravi et al. | 623/1 |
| 5,824,053 | 10/1998 | Khosravi et al. | 623/1 |
| 5,824,054 | 10/1998 | Khosravi et al. | 623/1 |
| 5,843,163 | 12/1998 | Wall | 623/1 |
| 5,910,168 | 6/1999 | Myers et al. | 623/1 |

OTHER PUBLICATIONS

EP 0 716 836, Tartaglia, et al., "Polymer Film for Wrapping a Stent Structure", 12/11/95.
PCT Publication WO 97/09007, Walter Anthony, "A Surgical Graft/Stent System", 3/13/97.

Primary Examiner—David H. Willse
Assistant Examiner—Suzette J. Jackson
Attorney, Agent, or Firm—Lyon & Lyon LLP

[57] ABSTRACT

A prosthesis is provided for treating aneurysms, occlusive disease of vessels and body organs, and arterio-venous fistulas, occurring in single and bifurcated lumens. The prosthesis comprises an expandable coiled sheet portion having a biocompatible graft, either a sheet or tube, affixed thereto along part or all of the circumference of the coiled sheet portion. The prosthesis has a small delivery profile, making it suitable for use in a variety of body vessels. Methods of making and deploying the prosthesis in single and bifurcated lumens are also provided.

25 Claims, 8 Drawing Sheets

METHODS OF MAKING AND USING COILED SHEET GRAFT FOR SINGLE AND BIFURCATED LUMENS

This application is a Continuation-in-Part of application Ser. No. 08/820,213, filed Mar. 18, 1997, now issued as U.S. Pat. No. 5,824,054, the disclosure of which is incorporated herein by reference.

FIELD OF THE INVENTION

The present invention relates to prostheses for treatment of aneurysms, arterio-venous fistulas, obstructive vascular disease and other applications. More specifically, the present invention relates to prostheses including coiled sheet portions having a biocompatible material affixed thereto which may be used in a variety of applications as an internal bandage.

BACKGROUND OF THE INVENTION

Millions of people worldwide are afflicted each year with vascular diseases, ranging from vascular obstructive disease, such as arteriosclerosis, to diseases that weakened the arteries or other vessels, resulting in potentially fatal aneurysms and arterio-venous fistulas. Arterio-venous fistulas commonly occur other than by progression of natural disease, for example, as a result of accidents and gun-shot wounds. Each of these diseases has lead to the development of specialized treatments ranging from minimally-invasive techniques to more conventional open surgical techniques.

For example, a health problem afflicting an older segment of the population is the occurrence of disease that weakens the arteries and other body vessels, developing into aneurysms that may rupture, often with fatal consequences. A conventional treatment of aneurysms, especially those occurring in the abdominal aorta, has involved invasive surgery to resect and remove the diseased body vessel and replace it with either a native vessel, harvested from elsewhere in the body, or a synthetic graft material. Such treatments typically pose a major risk to the patient's health, and frequently cannot be undertaken at all, if (as is common) the patient is in poor health.

A number of vascular prostheses have therefore been developed that permit a synthetic graft to be placed transluminally within the aneurysm, to isolate the aneurysm from fluids flowing in the body vessel and which relieve pressure from the aneurysm. These previously known vascular prostheses generally anchor a tubular synthetic graft inside the body vessel, on either end of the aneurysm, using a stent, as described, for example, in U.S. Pat. No. 5,078,726 to Kreamer and U.S. Pat. No. 5,219,355 to Parodi et al.

Similarly, U.S. Pat. No. 5,456,713 to Chuter and U.S. Pat. No. 5,275,622 to Lazarus describe stent-graft combinations, delivered transluminally, comprising a tubular graft having barbed self-expanding anchors secured by sutures to the ends of the tubular graft. U.S. Pat. No. 5,366,473 to Winston et al. describes a stent graft combination wherein a tubular graft has a self-expanding coiled sheet stent riveted to either end of the graft.

A drawback of the foregoing stent-graft systems is that they generally require a large access site (e.g., 16–22 Fr), which limits the applicability of such devices to larger vessels. Specifically, the graft material generally must be bunched or gathered to fit within the delivery system, as described in the above-mentioned Chuter, Winston et al. and Lazarus patents, but cannot be compacted within the delivery system, or problems may arise relating to unfurling of the graft during deployment. In addition, clinical testing of previously-known stent-graft combinations has revealed problems with inadequate sealing between the graft material and the anchors, and where the graft contacts the body lumen proximally and distally of the aneurysm.

Other arrangements for isolating aneurysms are also known. U.S. Pat. No. 4,577,631 to Kreamer describes a method of gluing a graft across an aneurysm using a biocompatible adhesive. U.S. Pat. No. 4,617,932 to Kornberg describes a bifurcated graft that is engaged to a vessel wall using hooks. U.S. Pat. No. 5,575,817 to Martin describes a bifurcated graft where an extension is added to one of the legs of the graft after a main body of the graft has been deployed. U.S. Pat. No. 5,211,658 to Clouse describes a stent-graft combination wherein a temperature activated skeleton is first deployed in a body lumen so that it spans an aneurysm; a graft then is affixed to the deployed skeleton. U.S. Pat. No. 5,405,379 to Lane describes a polypropylene sheet which is rolled into a coil, and permitted to self-expand within the body lumen so that it spans the aneurysm. U.S. Pat. No. 5,100,429 to Sinofsky et al. describes a coiled sheet stent including a layer of collagen-based material which is heated by an energy source so that it fuses to form a rigid structure.

Each of the foregoing arrangements has inherent disadvantages peculiar to their designs that makes the use of such designs impractical. These disadvantages range from the mechanical complexity of the Kreamer, Clouse and Sinofsky et al. designs, to the inability to obtain an adequate seal at ends of the device, as in the Kornberg, Martin and Lane devices.

With respect to treatment of obstructive vascular disease, a number of prostheses have been developed for intraluminal deployment. These devices, of which the Palmaz-Schatz stent sold by Cordis Corporation, Miami Lakes, Fla., is typical, treat obstructive disease, for example, in the coronary arteries, by retaining the patency of vessel following an angioplasty procedure. Most previously known prostheses designed to treat obstructive disease include a plurality of throughwall openings to promote cellular proliferation. A drawback of such designs, however, is that the openings may also promote re-formation of the obstruction over time.

Previously known techniques for treating arterio-venous fistulas, which permit oxygenated blood to be shunted from an artery directly to the venous system, typically involve open surgery. Thus, for example, a gun-shot victim, given the present state of the art, must undergo surgery to repair an arterio-venous fistula. The present state-of-the art lacks any devices which may be readily deployed, even on an interim basis, to prevent excessive blood loss while awaiting surgery.

In view of the foregoing, it would be desirable to provide a prosthesis for treating aneurysms, obstructive disease of vessels and body organs, and arterio-venous fistulas, that is simple in design and easily deployed.

It would further be desirable to provide a prosthesis for treating aneurysms, obstructive disease of vessels and body organs, and arterio-venous fistulas, that overcomes problems associated with the bulkiness of prior art stent-graft systems, and that can be readily scaled for use in a variety of vessels, thereby enabling treatment of disease in even very small body lumens.

It would further be desirable to provide a prosthesis for treating aneurysms, obstructive disease of vessels and body organs, and arterio-venous fistulas, that may be readily deployed in a bifurcated vessel.

It would still further be desirable to provide a prosthesis for treating aneurysms, obstructive disease of vessels and body organs, and arterio-venous fistulas, that provides an internal bandage, for example, that can stem blood loss through an arterio-venous fistula, or provide a positive seal at the ends of a graft to reduce bypass flow.

SUMMARY OF THE INVENTION

In view of the foregoing, it is an object of the present invention to provide a prosthesis for treating aneurysms, obstructive disease of vessels and body organs, and arterio-venous fistulas, that is simple in design and easily deployed.

It is another object of this invention to provide a prosthesis for treating aneurysms, obstructive disease of vessels and body organs, and arterio-venous fistulas, that overcomes problems associated with the bulkiness of prior art stent-graft systems, and that can be readily scaled for use in a variety of vessels, thereby enabling treatment of disease in even very small body lumens.

It is a further object of the present invention to provide a prosthesis for treating aneurysms, obstructive disease of vessels and body organs, and arterio-venous fistulas, that may be readily deployed in a bifurcated vessel.

It is a yet further object of the invention to provide a prosthesis for treating aneurysms, obstructive disease of vessels and body organs, and arterio-venous fistulas, that provides an internal bandage, for example, that can stem blood loss through an arterio-venous fistula, or provide a positive seal at the ends of a graft to reduce bypass flow.

These and other objects of the invention are accomplished by providing a prosthesis comprising a coiled sheet portion having biocompatible graft material affixed thereto, so that the graft material is at least partially wound within the coiled sheet portion when it is contracted to its delivery state. The graft material may comprise a sheet or tube that is affixed along a part or all of the circumference of the coiled sheet portion, and serves to alter flow to a portion of a body lumen in which the prosthesis is deployed. The graft may be affixed to an interior or exterior surface of the coiled sheet portion, or may comprise several layers. The prosthesis may be configured for use in a single or bifurcated organ or vessel.

In a preferred embodiment, the coiled sheet portion of the prosthesis comprises a mesh formed from a shape-memory alloy, such as a nickel-titanium alloy, that exhibits super-elastic behavior at body temperature. The coiled sheet preferably includes one or more rows of locking teeth along a longitudinal edge that interengage the mesh to retain the prosthesis at a desired expanded diameter. In addition, the mesh may include a plurality of radially outwardly directed projections along one or both ends that engage an interior surface of a body lumen.

The mesh of the coiled sheet may have a size suitable for use in smaller body arteries, such as the coronary arteries and carotid arteries, or may be scaled to accommodate larger vessels such as the abdominal aorta and iliac arteries. For larger vessels, the mesh of the coiled sheet may include articulations to assist in maneuvering the prosthesis through tortuous body passageways.

The graft material used in the prosthesis of the present invention may be either fluid impermeable, for example, for treating arterio-venous fistulas or semi-permeable, for example, to permit nourishment of vessel intima when treating occlusive vascular disease while reducing through-wall cell proliferation. The graft material may also be impregnated with one or more drugs to achieve to provide a desired effect. The graft material may also serve to reduce embolization of frangible material from the interior of body lumen following, for example, an angioplasty procedure.

In addition to the foregoing applications, a pair of prostheses constructed in accordance with the present invention may be advantageously employed, one at either end, for positively sealing the ends of a conventional tubular graft.

Methods of making and deploying the prosthesis of the present invention in single and bifurcated lumens are also provided. In accordance with these methods, the prosthesis is first deployed in a body lumen from a reduced delivery state. A dilatation element is then disposed within the prosthesis and expanded, thereby locking the prosthesis at an expanded diameter and positively sealing the graft material against the interior surface of the body lumen.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention provides prostheses for treating aneurysms, obstructive disease of vessels and body organs, and arterio-venous fistulas, that overcome the limitations of previously known minimally-invasive treatment systems. In particular, a prosthesis constructed in accordance with the present invention provides altered fluid flow through a section of a single or bifurcated body lumen with a device that is simple, yet elegant in design, easy to deploy, is readily scalable for use throughout the body, and provides the functionality of an internal bandage.

Figure 1:
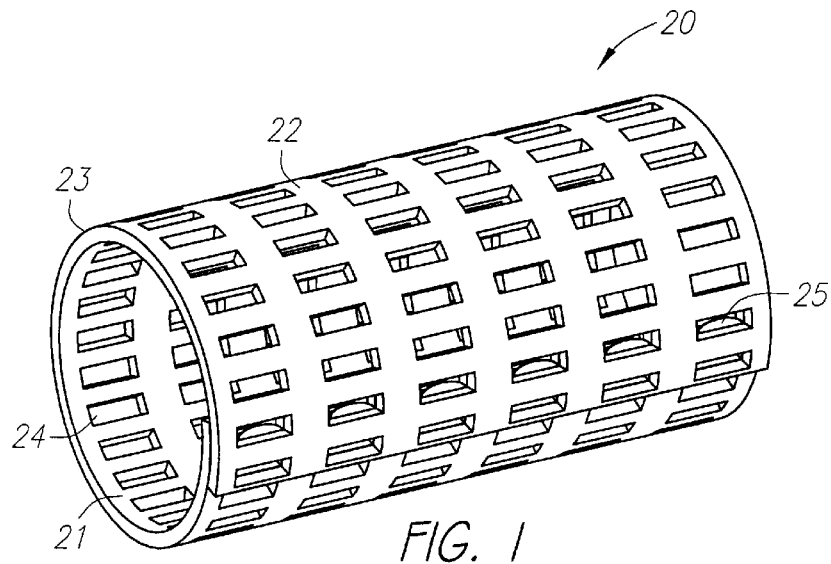
FIG. 1 is a perspective view of an illustrative prosthesis constructed in accordance present invention.

Referring to FIG. 1, illustrative prosthesis 10 constructed in accordance the present invention is described. Because prosthesis 20 includes certain features of both conventional coiled sheet stents, as described, for example, in U.S. Pat. No. 5,443,500 to Sigwart, incorporated herein by reference, and conventional synthetic tubular grafts, it is referred to hereinafter as a "graft stent."

Graft stent 20 comprises coiled sheet portion 21 including a resilient lattice or mesh onto which a layer of biocompatible graft material 22 has been affixed. Graft material 22 may have a permeability selected to address a particular application, and may be impregnated with one or more drugs to effect a desired treatment. Thus, for example, graft material 22 may be selected to be fluid impervious for arterio-venous fistula applications, but may be selected to be semi-permeable for applications where it is desired to permit nutrients to pass through the graft material, yet prevent cell proliferation therethrough. In yet other applications, the graft material may include a porosity sufficient to maintain a pressure differential between fluids disposed on either side.

Graft stent 20 preferably comprises a biocompatible material, such as a shape-memory alloy (e.g., nickel-titanium), while biocompatible graft material preferably comprises a PTFE or polyester fabric. Graft material 22 is affixed to coiled sheet portion 21 by any of the methods described hereinbelow, including biocompatible adhesive 23, by sintering, sutures, or any combination of thereof. Graft stent 20 may include a single coiled sheet portion sandwiched between multiple layers of graft material, or a single layer of graft material sandwiched between multiple coiled sheet portions.

Figure 2A:
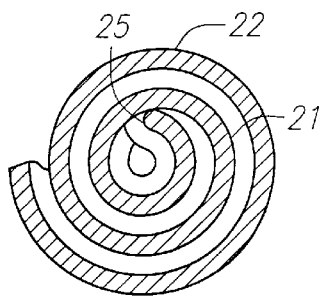
FIGS. 2A and 2B are end views showing the prosthesis of FIG. 1 in its contracted state and expanded state, respectively.
Figure 2B:
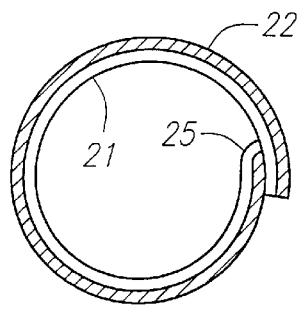

In the embodiment of FIG. 1, graft material 22 is affixed to coiled sheet portion 21 so that the graft material is wound within the series of overlapping turns of the coiled sheet portion when the prosthesis is wound to a reduced-diameter delivery (or "contracted") state, as shown in FIG. 2A. When the coil sheet portion is preferably biased to return to its larger-diameter deployed (or "expanded") state, as shown in FIG. 2B. In alternative embodiments, described hereinbelow with respect to FIG. 12, graft material 22 may comprise a solid tube, so that coiled sheet portion 21 is affixed within the tubular graft along a portion of the circumference of the coiled sheet portion.

Figure 3:
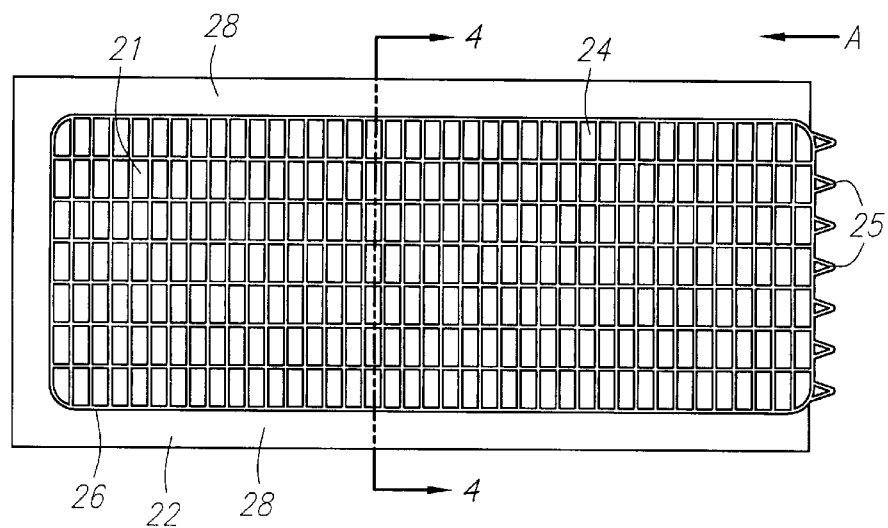
FIG. 3 is a plan view of the prosthesis of FIG. unrolled during a step of manufacturing.

Referring to FIG. 3, coiled sheet portion 21 of graft stent 20 is shown disposed on a sheet of graft material 22 during a step in the process of assembling graft stent 20. Coiled sheet portion 21 comprises a thin flat sheet of material, about 1.0 to 5.0 mils thick, which is formed into a lattice having a multiplicity of openings 24, for example, by die and punch, laser cutting or chemical etching. Openings 24 reduce the overall mass of the graft stent, provide some longitudinal flexibility when the graft stent is contracted, and may be used to enhance fixation of the graft material to the coiled sheet portion, as described hereinbelow. Openings 24 may be triangular-shaped, diamond-shaped, rectangular-shaped or circular-shaped, or any combination thereof, and are preferably arranged in a lattice that provides about 50% open space or more.

Alternatively, coiled sheet portion 21 be formed from a plurality of interwoven wires that are welded together around the circumference of the coiled sheet portion, such as described in U.S. Pat. No. 5,007,926 to Derbyshire, which is incorporated herein by reference. The intersections of the wires also may be welded together, and the sheet may be swaged to reduce its thickness.

In accordance with the present invention, coiled sheet portion 21 of graft stent 20 preferably includes one or more rows of teeth 25 adjacent to one edge that mate with openings 26 on an opposing overlapping edge of the coiled sheet. Teeth 25 lock the graft stent at a selected expanded diameter, as described in the incorporated Sigwart and Derbyshire patents. This locking action provides a tight seal of the graft material against the interior surface of the body lumen. When used to treat obstructive vascular disease, the tight seal serves to retain patency of the vessel and reduce the potential for embolization; for arterio-venous fistulas, the seal reduces shunted flow; for aneurysms, the seal reduces the risk of bypass flow around the edges of the graft stent. In a preferred embodiment, teeth 25 are sufficiently long to engage mating openings 26 so as to stretch any graft material covering openings 26, but without perforating that graft material.

Alternatively, graft stent 20 may be secured in place in the body lumen using a coiled sheet portion that retains several overlapping turns even in the expanded state, as described, for example, in U.S. Pat. No. 5,306,294 to Winston et al.

Coiled sheet portion 21 may be formed from any biocompatible material, such as a thermal shape-memory polymer or metal, super-elastic material such as a nickel-titanium alloy, or other biocompatible resilient material such as a stainless steel, tantalum, platinum or tungsten alloy. In a preferred embodiment, a nickel-titanium alloy is used that has an austenite transition temperature slightly below body temperature, so that the coiled sheet portion exhibits super-elastic behavior when deployed. Also in the preferred embodiment, the nickel-titanium coiled sheet portion is heat treated, using processes known in the art, for activating the shape-memory effect of the material so that the coiled sheet portion has an expanded diameter in the austenite phase.

Coiled sheet portion 21 of graft stent 20 may be formed in a variety of sizes depending upon the intended application. For example, a graft stent for use in the treatment of aneurysms of the abdominal aorta may require a length of 8–12 cm and an expanded diameter of 2–4 cm, while a graft stent for use in a main branch artery, or the iliac arteries, may require a length of 2–8 cm and an expanded diameter of 8–12 mm. Of course, graft stents for use in other vessels, for example, to treat A-V fistulas or obstructive disease, may be smaller. While graft stents for use in vessels under about 2.0 cm may employ a single coiled sheet portion 21 (as shown in FIG. 3), in accordance with the present invention, multiple coiled sheet portions also may be used to built longer graft stents. In addition, as described hereinafter, the graft stent of the present invention may be advantageously used to anchor a conventional tubular graft in place across a large aneurysm.

Referring now to FIGS. 3 and 4A–4F, the process of making a graft stent in accordance with the present invention is described. While the graft stent of FIG. 3 comprises one coiled sheet portion 21, several such coiled sheet portions 21 may be laid side-by-side, thereby providing a graft stent with an overall length about several times that of graft stent 20 of FIG. 3. Coiled sheet portion 21 is disposed on a sheet of biocompatible graft material 22, such as PTFE or polyester fabric. The coiled sheet portion 21 is then fastened to the sheet of graft material using one or more of the methods described hereinbelow. Any excess portion of the sheet may then be trimmed away, for example, with a razor knife to form the completed graft stent. The graft stent is then sterilized, for example, using a conventional ethylene oxide process.

Figure 4A:
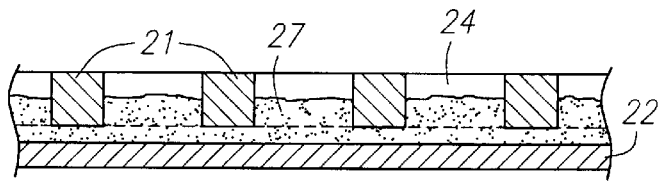
FIGS. 4A–4F are cross-sectional views taken along view line 4—4 of FIG. 3 and a plan view (FIG. 4D) of alternative embodiments of a prosthesis constructed in accordance with the present invention.

In a first method of construction, shown in FIG. 4A, coiled sheet portion 21 is coated with a thin layer of biocompatible adhesive 27 (for example, with a brush or by dipping), such as a liquid polyurethane resin or epoxy. Adhesive 27 preferably remains flexible when dry. While the adhesive is still wet, coiled sheet portion 21 is positioned on graft material 22 as shown in FIG. 3. When adhesive 27 dries, it bonds coiled sheet portion 21 to graft material 22. If several unconnected coiled sheet portions are employed, adhesive 27 also provides a joint between the neighboring coiled sheet portions. Excess portions 28 of graft material 22 (for example, around the edges of coiled sheet portion 21) may then be trimmed to complete assembly of the graft stent.

When finished, a graft stent constructed by the above-described process has a cross-section similar to that depicted in FIG. 4A, in which adhesive 27 forms a layer, preferably about 0.1 mil thick, that bonds graft material 22 to the outer surface of coiled sheet portion 21. Adhesive 27 also extends slightly into openings 24. Applicant has observed that a layer of polyurethane adhesive, employed as described above with respect to FIGS. 3 and 4A, provides good column strength in a graft stent built from a plurality of separate coiled sheet portions. Accordingly, the graft stent of the present invention may be built up to any desired length using the process described hereinabove.

Figure 4B:
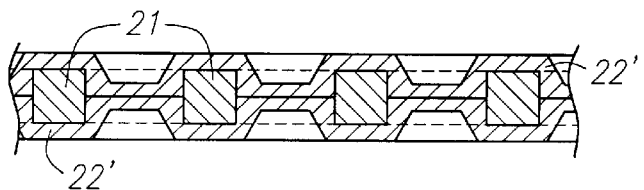

In FIG. 4B, a alternative method of making a graft stent by sintering graft material to a coiled sheet portion is described. In this embodiment, coiled sheet portion 21 is sandwiched between two layers of a biocompatible graft material 22', such as PTFE. The assembly is then heated to raise the graft material to a temperature at which the two layers contact one another through the multiplicity of openings 24, and fuse or sinter together, thereby forming a waffle shape. Pressure may be applied to the assembly during the heating process to accelerate the fusing or sintering step. In addition, sutures or a thin layer of biocompatible adhesive may be employed to retain the assembly together prior to the heat treatment. Consequently, the two layers of graft material 22' disposed on the opposite sides of coiled sheet portion 21 form a single fused layer within which coiled sheet portion 21 is embedded.

Figure 4C:
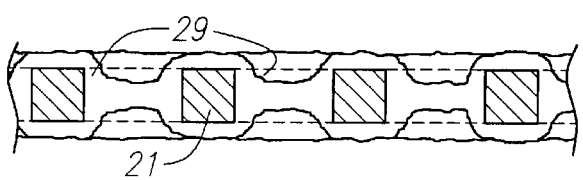

In FIG. 4C another method of making a graft stent is described. In this method, the coiled sheet portion is dipped into a liquid polymer, such as urethane. The coiled sheet portion is then withdrawn from the liquid polymer so that the liquid forms a film 29 extending across the multiplicity of openings 24 in the coiled sheet portion 21. The coiled sheet portion may then be disposed on a section of graft material, as in the first method described above, so that the coated stent portion adheres to the graft material. Alternatively, the liquid polymer film 29 may be permitted to air dry without being bonded to a graft portion. In this latter embodiment, the polymer film itself serves as the graft material.

Figure 4D:
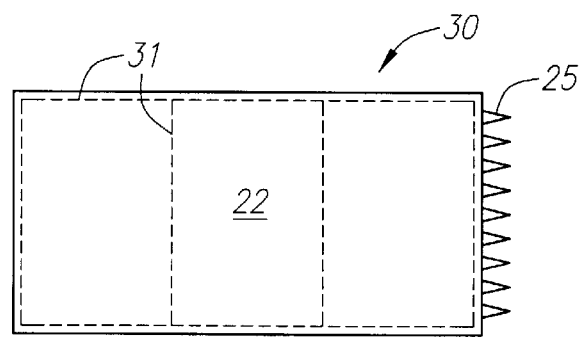

With respect to FIG. 4D, yet another method of making a graft stent of the present invention is described. In the embodiment of FIG. 4D, graft stent 30 is formed by sewing or suturing coiled sheet portions 21 to graft material 22, with stitches or sutures 31 extending through some of the multiplicity of openings of the coiled sheet portion. In a preferred method, the coiled sheet portions are first dipped in a biocompatible adhesive and adhered to the graft material to retain the graft material in a desired relation to the coiled sheet portion. Biocompatible stitches or sutures 31 are then applied by machine or by hand along the edges and at intervals along the graft material to affix the graft material to the coiled sheet portion.

Figure 4E:
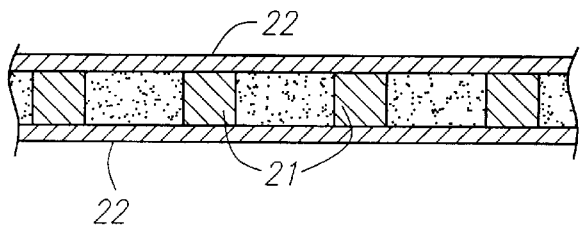

With respect to FIG. 4E, a graft stent is formed by first sewing two pieces of graft material 22 together along three sides to form a "pillow case" structure. Coiled sheet portion 21 is then inserted within the pillow case structure, so that the edge carrying the locking teeth projects from the open edge. The graft material is then affixed to coiled sheet portion 21 with single machine-stitched or hand-stitched seam. The embodiment of FIG. 4D enables the graft material to experience some lateral movement with respect to the coiled sheet portion, which may be desirable in certain circumstances.

Figure 4F:
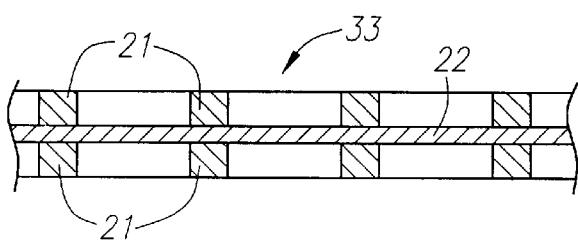

In FIG. 4F, a yet further alternative embodiment is the graft stent of the present invention is described. Graft stent 33 comprises a single sheet of graft material 22 sandwiched between two coiled sheet portions 21. Coiled sheet portions 21 may be glued together by a suitable biocompatible adhesive, or stitched or sutured to one another, thereby trapping the graft material in between the coiled sheer portions. Alternatively, one of the coiled sheet portions may include projections, while the other includes mating sockets to accept the projections, thereby retaining the assembly together. The embodiment of FIG. 4F of the invention is particularly well-suited for addressing problems relating to in-situ swelling of graft material in prior art grafts, because swelling of the graft material is limited by the coiled sheet portions.

Advantageously, with respect to the above-described embodiments of the present invention, because the lattice of the coiled sheet portion does not undergo longitudinal or radial distortion during deployment, the graft material of the graft stent of the present invention is not subjected to stress or distortion that could lead to perforation of the graft material during deployment and use.

In addition, as a further step of the manufacture of any of the above embodiments of the graft stent of the present invention, the graft material may be impregnated with one or more drugs to achieve a desired treatment goal. For example, the outer surface of the graft stent may coated with an anti-heparin drug, such as Proamine, to enhance clotting of blood captured outside the graft stent (for example, to promote thrombosis within an aneurysm or to prevent embolization of frangible material from the vessel wall), and may include a coating of a heparin-type compound on the inner surface of the graft stent to reduce the risk of thrombosis within the vessel.

Figure 5A:
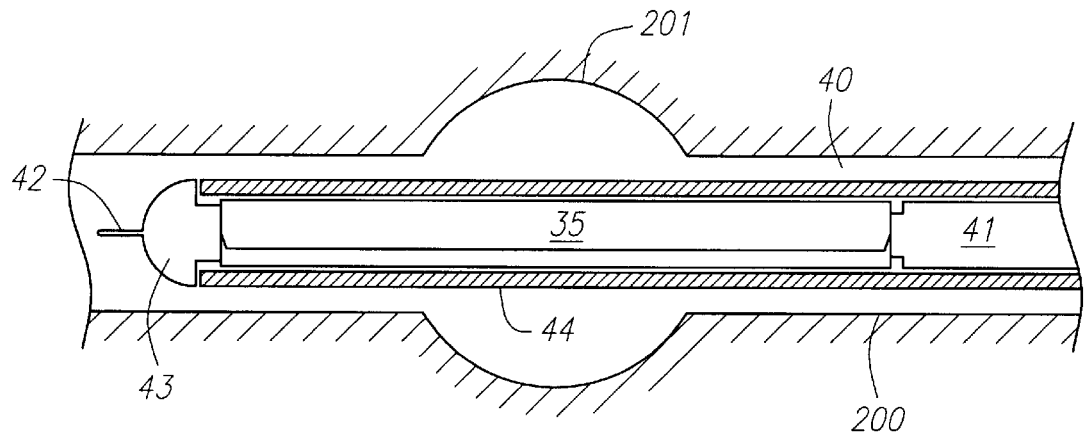
FIGS. 5A–5C are views showing the steps of deploying the prosthesis of FIG. 1 to span an idealized aneurysm in a single lumen.
Figure 5B:
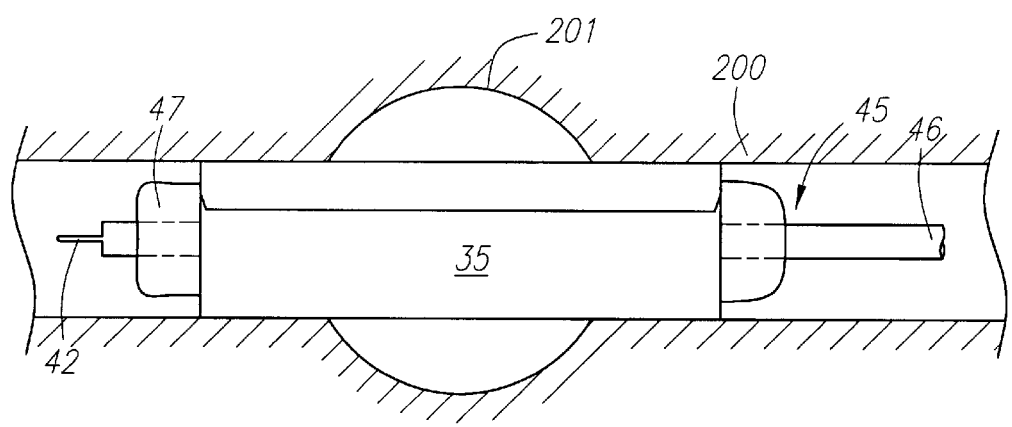
Figure 5C:
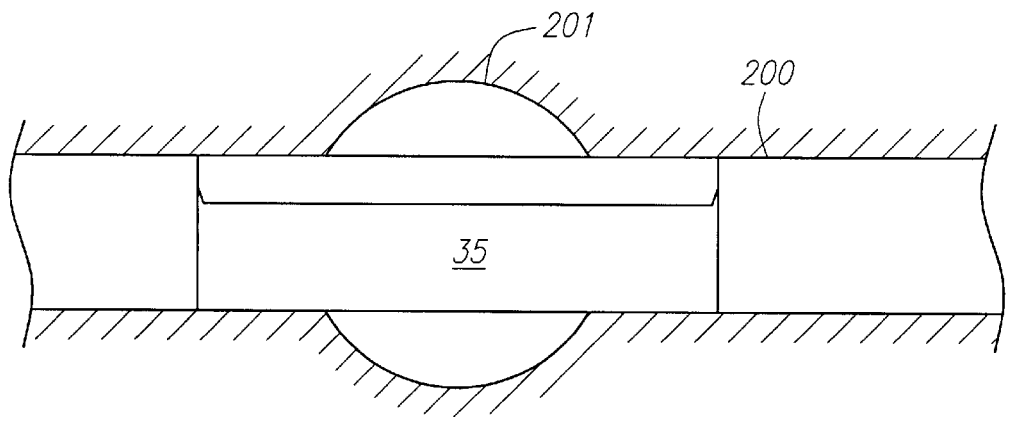

Referring now to FIGS. 5A–5C, the steps of deploying the graft stent of the present invention to treat an idealized aneurysm in a single lumen portion of a vessel are described. It will be understood, however, that the steps of deploying a graft stent to treat an A-V fistula or obstructive disease of a vessel or body-organ apply equally.

Graft stent 35 is formed using the components and the methods of manufacture described hereinabove. The graft stent is then rolled about a mandrel in a direction indicated by arrow A in FIG. 3 (so that teeth 25 are inside the coil) to a contracted state for delivery. As of course will be understood by one skilled in the art, graft stent is contracted to the reduced diameter by winding the coiled sheet portion to form a series of overlapping turns. The contracted graft stent is then loaded into a sheath for delivery, as described, for example, in Sigwart U.S. Pat. No. 5,443,500 or Garza et al. U.S. Pat. No. 4,665,918, the entireties of which are incorporated herein by reference, which retains the graft stent in its contracted diameter.

In FIG. 5A, graft stent 35 is shown rolled to its contracted state and disposed within delivery system 40, such as described in the above-incorporated Garza et al. patent. For clarity, the detail of the lattice of graft stent 35 is omitted in FIGS. 5A–5C. Delivery system 40 includes catheter 41 having a central lumen for accepting guide wire 42, nose cone 43 and outer sheath 44. Delivery system 40 is inserted into body lumen 200 to be treated, for example, having aneurysm 201, through a major vessel along guide wire 42, as is well-known in the art, until the mid-point of the graft stent is located within aneurysm 201.

Once the location of delivery system 40 is established, for example, using fluoroscopy and standard angiographic techniques, outer sheath 44 of the delivery system is retracted to release graft stent 35 into body lumen 200 so that it spans aneurysm 201. When released from outer sheath 44, graft stent 35 unwinds at least partially to conform to the diameter of the body lumen.

With respect to FIG. 5B, mechanical expander 45, which may be a balloon catheter 46 carrying compliant balloon 47, is transluminally inserted within graft stent 35 and expanded. As balloon 47 expands, graft stent 35, the teeth on the inner edge ratchet across the openings in the opposing edge of the graft stent, so that the graft is locked at progressively larger diameters (as seen in FIG. 2B). Balloon 47 may be inflated, for example, while visualized with conventional fluoroscopic and angiographic techniques, until graft stent 35 is expanded to a diameter at which the teeth of the coiled sheet portion positively lock the graft stent against the healthy portions of body lumen 200 and prevent bypass flow through aneurysm 201.

Once graft stent 35 has been locked into position within body lumen 200, balloon 47 is contracted, and balloon catheter 46 is withdrawn from the body lumen. Because the teeth interengage with the openings on the opposing overlapping edge of the graft stent, graft stent 35 retains the expanded diameter attained during the step of the balloon expansion, as illustrated in FIG. 5C, and does recoil elastically to the shape assumed when initially released from outer sheath 44.

Importantly, because graft stent 35 is elastically expanded by unwinding from its rolled position, no stress is applied to the graft material, thereby reducing the risk of perforation. Moreover, since the graft stent of the present invention preferably comprises a coiled sheet portion formed from a super-elastic shape memory alloy, such as a nickel-titanium alloy, the graft stent may be conformed to a wide range of body lumen diameters while providing adequate radial strength.

As also will be apparent to one of skill in the art, the graft stent of the embodiment of FIG. 1 is distinguished from other previously known stent graft combinations in that while the graft material covers the stent, no bunching or gathering of the graft material occurs when the graft stent is contracted to its delivery diameter. Instead, the graft material is wound along with the coiled sheet portion of the graft stent to a contracted diameter for delivery, and features a longitudinal seam that is closed only when the graft stent is fully deployed. Accordingly, the graft stent of the present invention may be contracted to extremely small diameters, enabling the use of grafts in vessels not accessible using previously known stent graft delivery systems.

Figure 6:
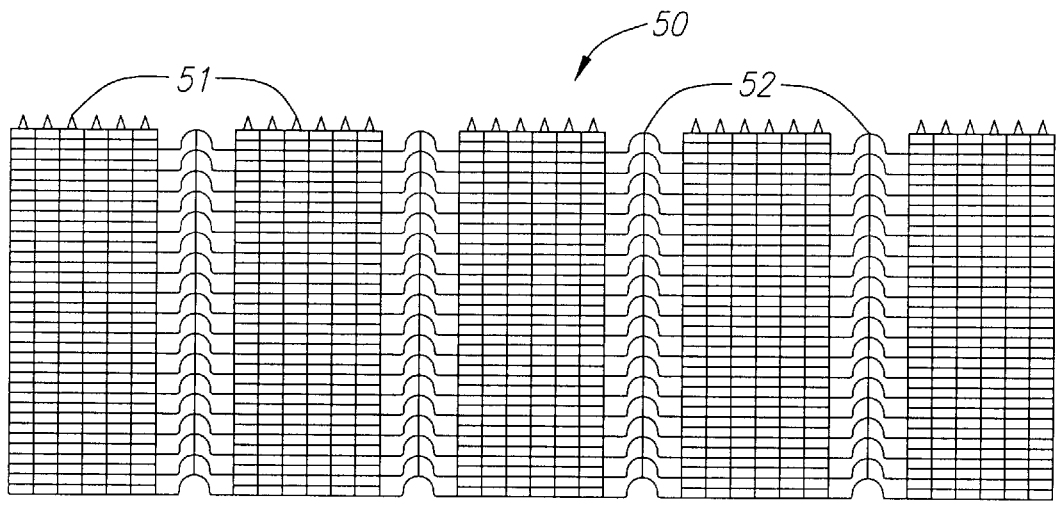
FIGS. 6 and 7 are plan views of alternative articulated mesh designs suitable for use with the prosthesis of the present invention.
Figure 7:
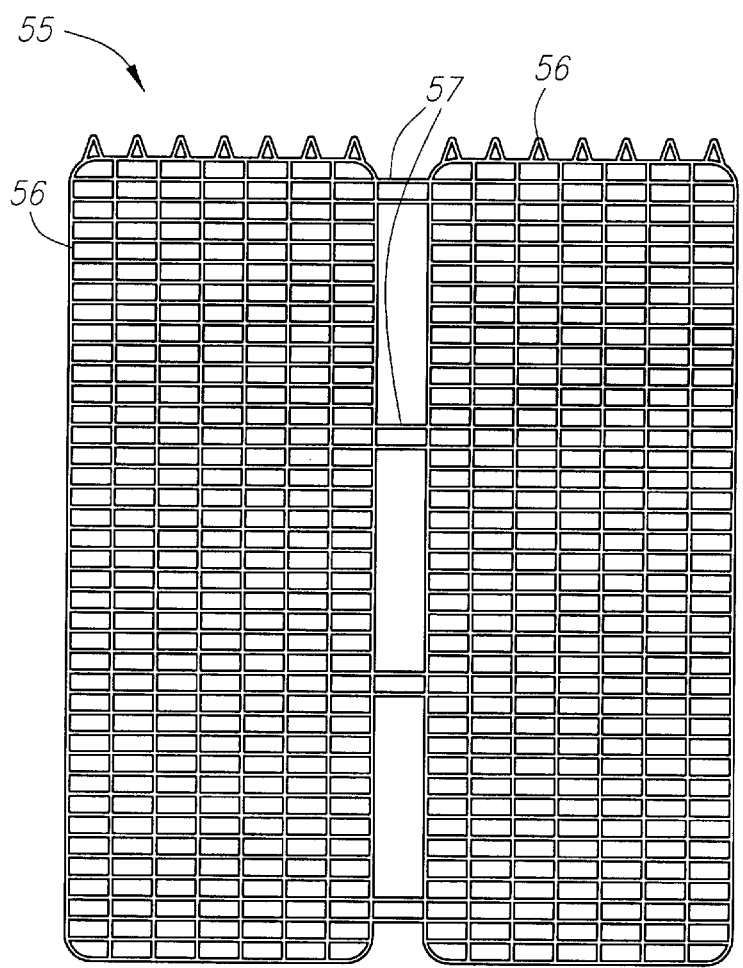

Referring now to FIGS. 6 and 7, alternative embodiments of the coiled sheet portion of the inventive graft stent are described. Coiled sheet portion 50 of FIG. 6 comprises a plurality of elements 51 joined by serpentine articulations 52, while coiled sheet portion 55 of FIG. 7 comprises a plurality of elements 56 joined by linear articulations 57. Coiled sheet portions 51 and 56 illustratively employ the lattice design of coiled sheet portion 11 of FIG. 2. Articulations 52 and 57 are contemplated to give coiled sheet portions 50 and 55, respectively, greater flexibility for passing through tortuous body lumens.

Figure 8B:
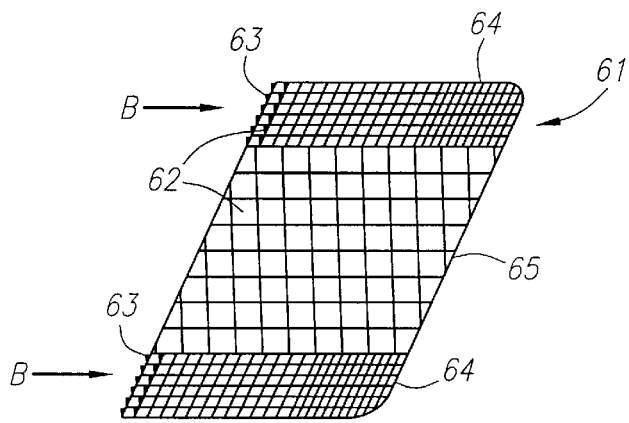
FIGS. 8A and 8B are perspective and plan views, respectively, of a prosthesis employing a coiled sheet mesh designed for large vessels, in which the detail of FIG. 8B has been omitted from FIG. 8A for clarity.
Figure 8A:
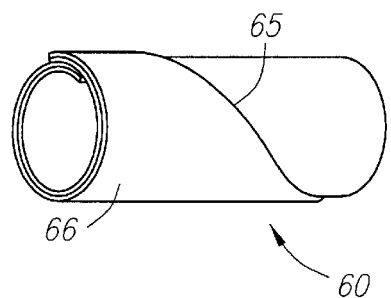

FIGS. 8A and 8B provide a further alternative for creating graft stent 60 for use in larger vessels. FIG. 8B depicts coiled sheet portion 61 having a variable geometry of openings 62 in the mesh lattice. The mesh shown is expected to provide greater flexibility for a large graft stent, for example, having a length about 10 cm and a diameter of 2–4 cm. Coiled sheet portion 61 includes teeth 63 that mate with openings 64 in opposing overlapping edge 65 of coiled sheet portion 61.

Coiled sheet portion 61 has suitable graft material 66 affixed to its outer surface, using the methods of manufacture described hereinabove. When rolled in the direction indicated by arrows B in FIG. 8B, graft stent 60 forms the tubular member shown in FIG. 8A (detailed omitted), wherein overlapping edge 65 of the graft stent spirals around the outer surface of the prosthesis. Graft stent 60 of FIGS. 8A and 8B is deployed in a manner similar to that described above with respect to FIGS. 5A to 5C. It is contemplated that the spiral nature of the overlapping edge will advantageously distribute radial expansive forces around the circumference of the graft stent, thus reducing the risk of buckling.

Figure 9A:
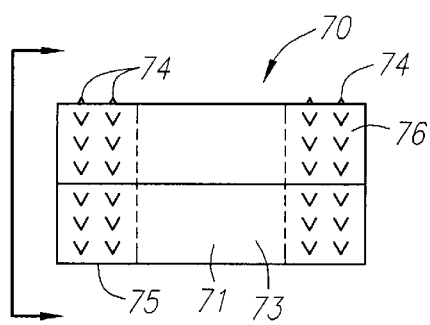
FIGS. 9A and 9B are front and side elevation views, respectively, of a further alternative embodiment of the prosthesis of the present invention.
Figure 9B:
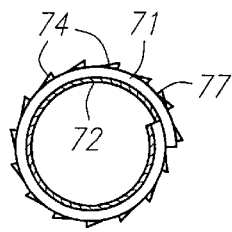
Figure 10:
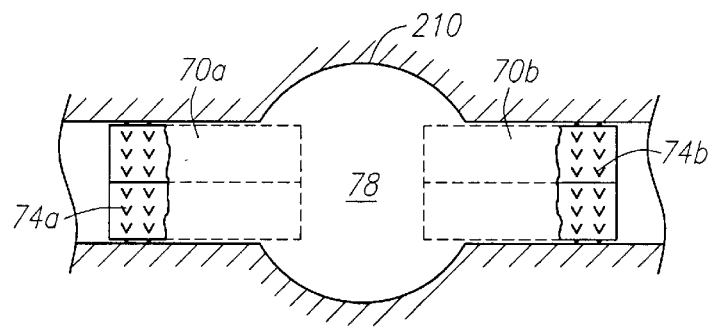
FIG. 10 is a side view showing implantation of a tubular graft with the prosthesis of FIG. 9A.

Referring now to FIGS. 9A and 9B, an further alternative embodiment of the present invention is described with respect to graft stent 70. In FIGS. 9 and 10 the lattice detail of coiled sheet portion 71 has been omitted for clarity. Graft stent 70 preferably has graft material 72 affixed to an interior surface of the coiled sheet portion 71 in mid-region 73. Coiled sheet portion 71 includes rows of radially projecting barbs 74 on its outer surface in regions 75 and 76 adjacent the ends of the graft stent.

Barbs 74 are oriented so that they freely permit expansion of the coiled sheet portion, but engage the interior of the body lumen to resist contraction of the stent due to external radial compressive force. Barbs 74 of graft stent 70 preferably are formed as part of the etching or punching process during formation of the coiled sheet stent portion of the graft stent. Interlocking teeth 77 preferably are sharp enough to pierce and protrude through graft material 72 when the graft stent 70 is locked into position by a dilatation member.

In FIG. 10, a pair of graft stents 70a and 70b are shown disposed in tubular graft 78 to seal the tubular graft to the healthy tissue proximal and distal of aneurysm 210. Tubular graft 78 may be a previously known fabric graft, constructed, for example, from a polyester material. Graft stents 70a and 70b are "directional" in the sense that graft stent 70a preferably has barbs 74a disposed on its outer surface near its left hand end, whereas graft stent 70b has barbs 74b disposed on its outer surface near its right hand end. It is expected that graft stents 70a and 70b of the present invention will provide positive sealing at the proximal and distal ends of the tubular graft which has been unattainable heretofore.

Figure 11A:
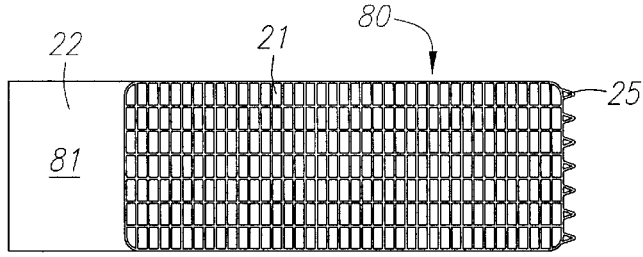
FIGS. 11A and 11B are plan and side views, respectively, of another alternative embodiment of the prosthesis of the present invention.
Figure 11B:
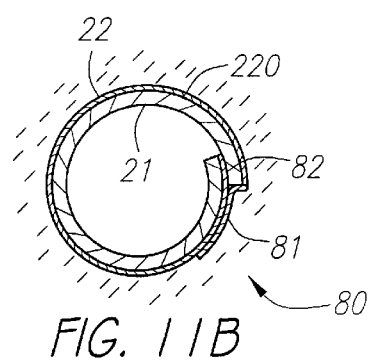

With respect to FIGS. 11A and 11B, yet another alternative embodiment of a graft stent of the present invention is described. Graft stent 80 is similar in construction to the prosthesis of FIG. 1, except that during the manufacturing process, a length of graft material 22 is left along the exterior edge of the coiled sheet portion 21 to form flap 81. As seen in FIG. 11B, when graft stent 80 is deployed in body lumen 220, flap 81 overlaps longitudinal seam 82 in of the graft stent for part of an additional turn, for example, one-quarter to one-half the deployed circumference.

In accordance with the present invention, flap 81 of graft stent 80 performs three functions. First, the flap serves to seal longitudinal seam 82 to prevent leakage. Second, flap 81 serves to anchor the mid-section of the coiled sheet portion 21 to prevent bowing of the midsection of the coiled sheet when deployed. Third, the length of the flap may be adjusted to control the rate at which the coiled sheet portion expands when the graft stent is deployed. In particular, if flap 81 is selected to have a length of, for example, one-half of the deployed circumference, it is expected that flap 81 will provide a sliding resistance as the coiled sheet portion unwinds, thereby controlling the rate at which the coiled sheet is deployed.

Figure 12:
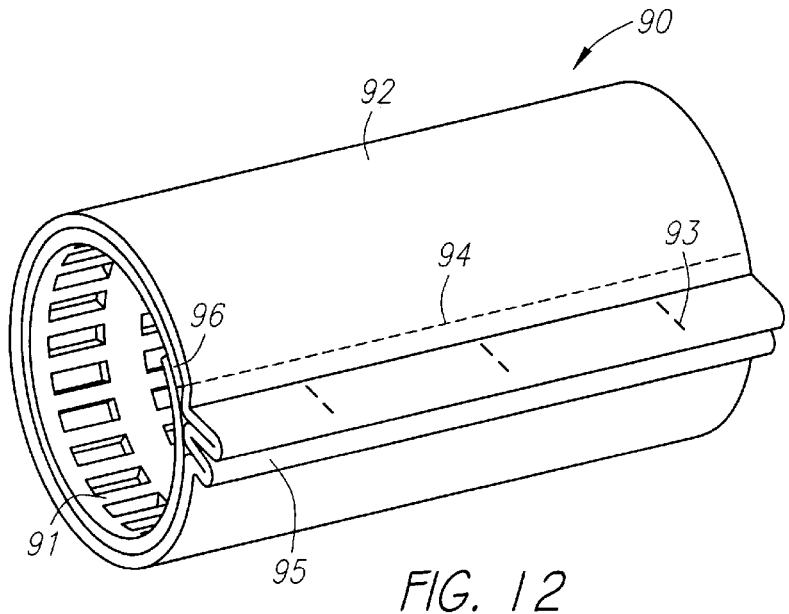
FIG. 12 is a perspective view of another a still further alternative embodiment of a prosthesis constructed in accordance present invention.
Figure 13A:
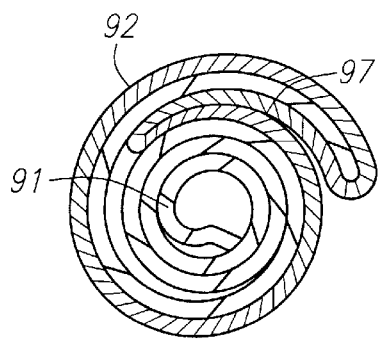
FIGS. 13A and 13B are end views showing the prosthesis of FIG. 12 in its contracted state and expanded state, respectively.
Figure 13B:
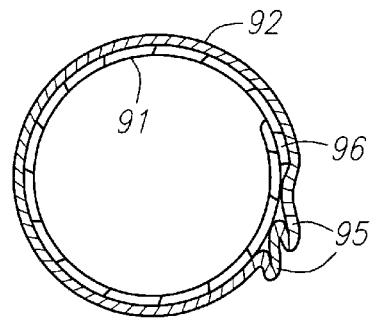

Referring to FIGS. 12, 13A and 13B, a still further embodiment of a graft stent is described. Graft stent 90 includes coiled sheet portion 91 and graft material 92 that has its edges sewn together to form a tube. Elastic filaments 93 may be disposed in the region of the tube adjacent longitudinal seam 94 in coiled sheet portion 91 so that the slack portion of the tube forms folds 95. When deployed in a vessel, folds 95 are crushed against the vessel wall by coiled sheet portion 91.

To enable stent graft 90 to be wound to its contracted state, graft material 92 is affixed to the exterior surface of coiled sheet portion 91 along only the part of the circumference of the coiled sheet portion nearest edge 96. Thus, when wound to its contracted state, coiled sheet portion 92 is only partly wound within the overlapping turns of the coiled sheet portion, and doubles back on itself in region 97. Alternatively, the non-affixed portion of graft material 92 may be wound against the coiled sheet portion in a direction opposite to that of the coiled sheet portion.

As shown in FIG. 13B, when graft stent 90 is deployed to its expanded state, elastic filaments 93 keep slack portions of the tube arranged in folds 95, thus permitting the graft material to be expanded when coiled sheet portion 91 is locked in position as described hereinabove with respect to FIGS. 5A–5C. It is expected that by forming graft material 92 into a tube (and thus eliminating the longitudinal seam in the embodiment of FIG. 1), the tendency of edge 96 to buckle outward when unsupported over long distances will be reduced. The embodiment of FIG. 12 is also expected to provide the advantages perceived for the embodiment of FIGS. 11A and 11B, described hereinabove.

Figure 14A:
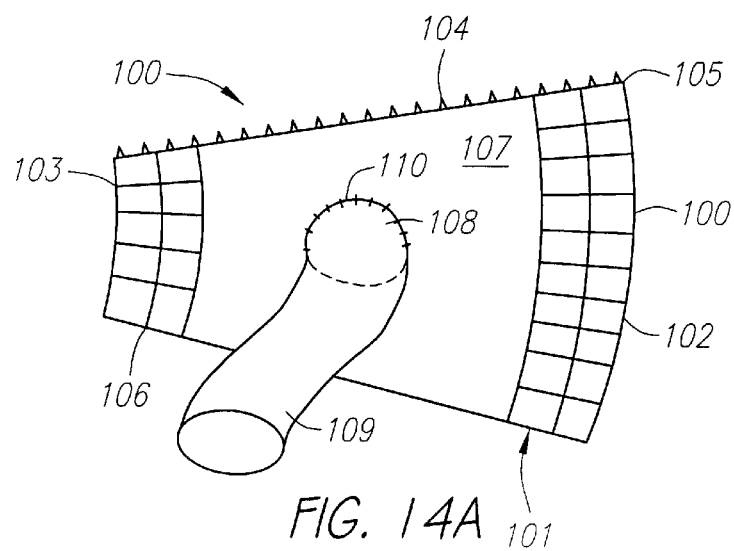
FIGS. 14A and 14B are, respectively, views of an embodiment of the prosthesis suitable for treating a bifurcated lumen in an uncoiled state, and as deployed in a bifurcated lumen.
Figure 14B:
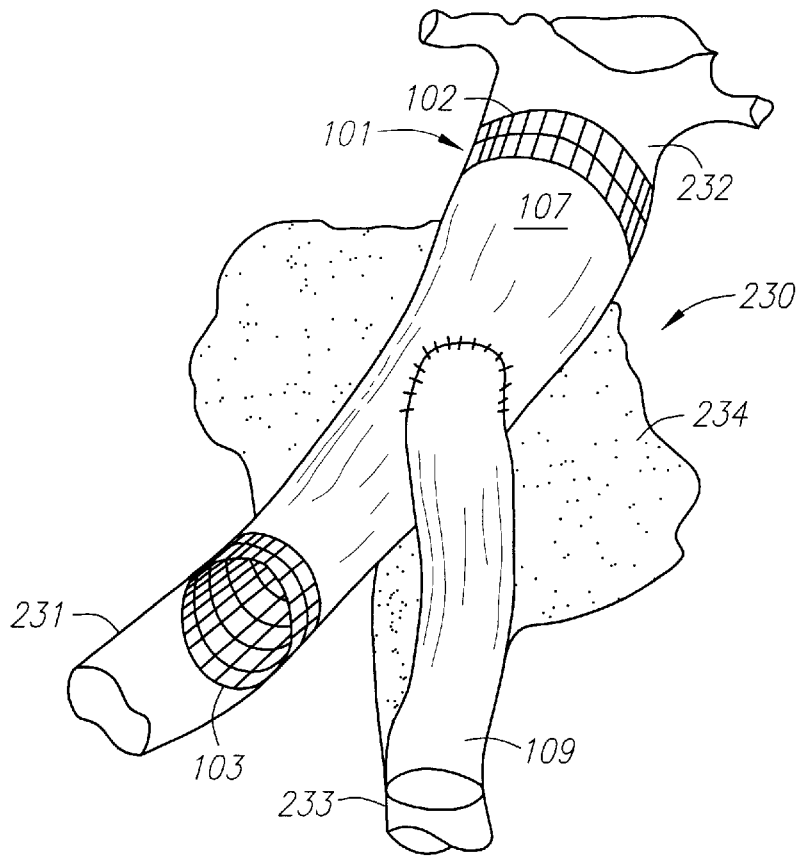

Referring now to FIGS. 14A and 14B, an embodiment of a graft stent suitable for use in treating a bifurcated lumen, illustratively the abdominal aorta, is described. In FIG. 14A, coiled sheet portion 101 of graft stent 100 forms a segment of an annulus having large circumference edge 102 and small circumference edge 103. When rolled to its coiled expanded state, coiled sheet portion 101 forms a conical shape. Teeth 104 are arranged along inner edge 105 of coiled sheet portion, and engage openings along edge 106 in the expanded state. Graft material 107 is affixed to coiled sheet portion 101 as described hereinabove, and includes an opening 108. Tubular graft 109, which may comprise a biocompatible material, is affixed to graft material 107 in alignment with opening 108, for example by stitches 110.

As shown in FIG. 14B, graft stent 100 may be coiled to form a tube and deployed to its expanded state in bifurcated lumen 230 so that small circumference edge 103 is disposed in branch 231 and large circumference edge 102 is disposed in trunk 232. When deployed, as described hereinbelow, tubular graft 109 extends into branch 233 of bifurcated lumen 230, thereby excluding aneurysm 234 from the flow path.

Figure 15A:
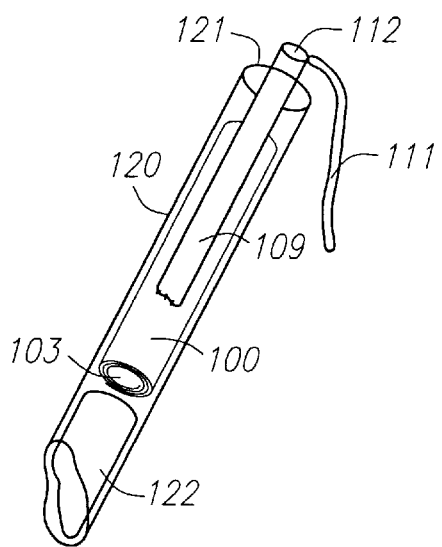
FIGS. 15A and 15B are views showing the steps of deploying the prosthesis of FIGS. 14 to treat an aneurysm in a bifurcated lumen.
Figure 15B:
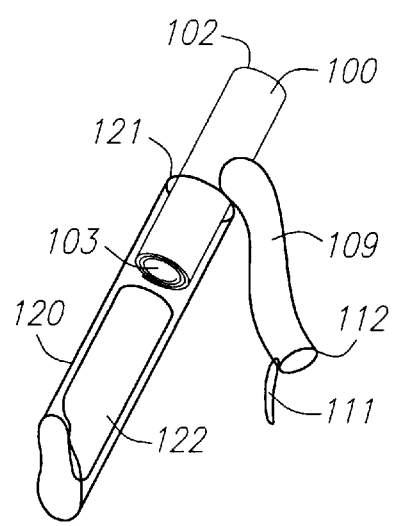

With respect to FIGS. 14B, 15A and 15B, deployment of graft stent 100 is described. In FIGS. 15A and 15B, to enhance clarity, the details of the coiled sheet portion have been omitted and delivery sheath 120 is illustrated as being transparent. In FIG. 15A, graft stent 100 is shown disposed in delivery sheath 120 and is coiled to its contracted state. Tubular graft 109 is folded against graft stent 100 so that the end of the tubular graft is located near distal end 121 of delivery sheath 120. Suture 111 forms a loop through end 112 of tubular graft 109. Push rod 122 is disposed in delivery sheath 120 and retains the graft stent 100 in position while delivery sheath 120 is retracted proximally.

Delivery system 120 as depicted in FIG. 15A is inserted transluminally into the bifurcated lumen via one of the branches. For example, in FIG. 14B, delivery system 120 may be inserted via branch 231 (e.g., the left femoral artery), so that distal end 121 of delivery system 120 is disposed in trunk 232 of the bifurcated lumen 230. A guide wire may then be inserted via the contralateral branch 233 and used to snare suture 111. Suture 111 is then brought out through the contralateral branch access site.

With respect to FIG. 15B, push rod 122 is used to retain graft stent 100 in a predetermined position relative to bifurcated lumen 230, while delivery sheath 120 is retracted. This step permits tubular graft 109 to be fully exposed, so that it does not contact distal end 121 of delivery system 120. Suture 111 is used to manipulate tubular graft 109 into position in branch 233. Push rod 122 is again employed to maintain graft stent 100 in position while delivery sheath 120 is fully withdrawn.

Once delivery sheath 120 is withdrawn, coiled sheet portion 101 of the prosthesis expands to its expanded state. As described hereinabove with respect to FIG. 5B, a balloon dilatation system may then be inflated within coiled sheet portion 101 to lock graft stent 100 in position. The loop formed by suture 111 is then cut, and the suture material pulled through end 112 and out of the patient's body. When fully deployed, the graft stent excludes aneurysm 234 from the flow path of bifurcated lumen 230. In addition, an additional previously known stent, such as described in the above incorporated Sigwart patent, may be employed to affix end 112 of graft stent 100 is place.

Figure 16A:
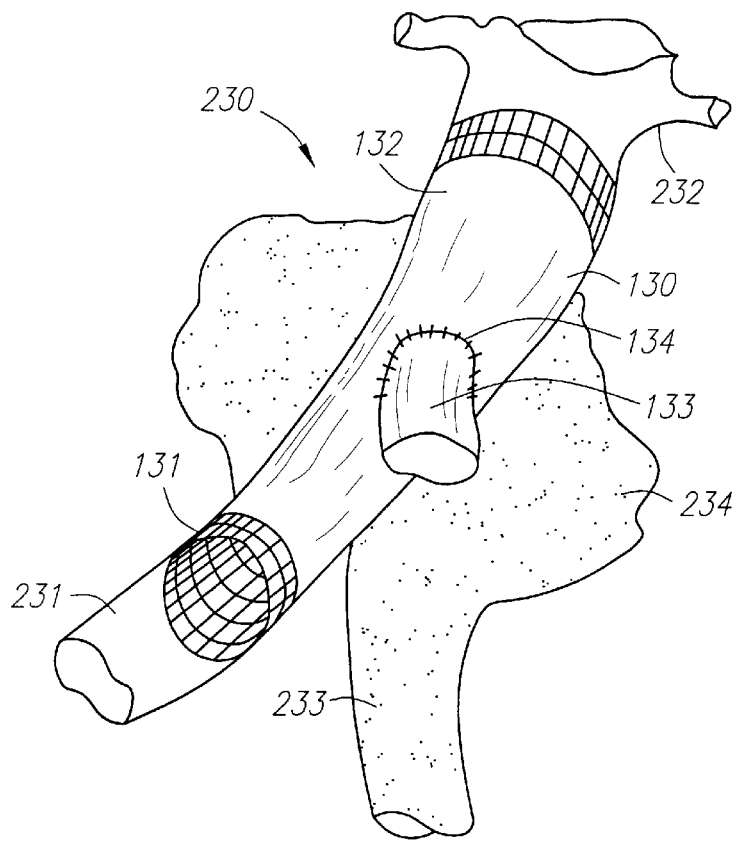
FIGS. 16A and 16B are views showing the steps of deploying an alternative embodiment of the prosthesis of FIGS. 14 to treat an aneurysm in a bifurcated lumen.
Figure 16B:
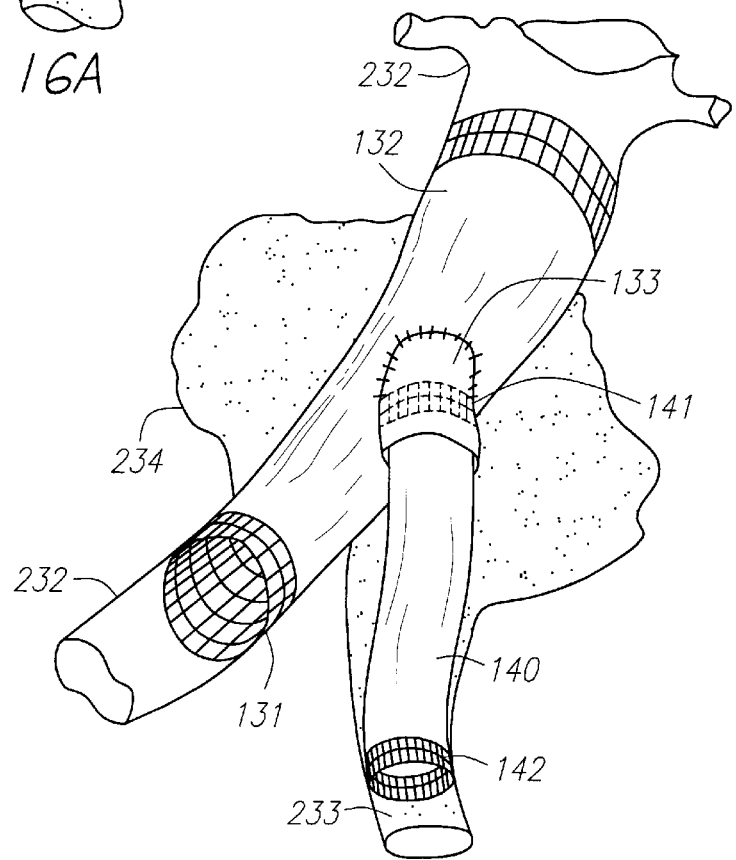

Referring to FIGS. 16A and 16B, an alternative to the embodiment of FIG. 14 is described for treating an aneurysm in bifurcated lumen 230. Graft stent 130 comprises a rectangular or annular segment-shaped coiled sheet portion 131 having graft material 132 affixed to it using any of the processes described hereinabove. Instead of tubular graft 109 of the embodiment of FIG. 14, however, graft stent 130 includes docking neck 133 attached in alignment with the opening in graft material 132 via sutures 134. Docking neck 133 may include radiopaque filaments embedded within it so that graft stent 130 can be deployed with docking neck oriented in alignment with branch 233, as determined, for example, by fluoroscopy.

A delivery system similar to that of FIG. 15A is first used to deploy graft stent 130 so that it extends from trunk 232 to branch 231 of bifurcated lumen 230. After graft stent 130 has been locked into position, a second delivery sheath containing graft stent 140, constructed as described with respect to FIG. 1 or FIG. 12, is inserted through contralateral branch 233. Graft stent 140 is then deployed so that distal end 141 is disposed in docking neck 133 of graft stent 130 and proximal end 142 is disposed in branch 233. Graft stent 140 is deployed as previously described. Accordingly, graft stents 130 and 140 may be assembled in-situ to exclude aneurysm 234 in bifurcated lumen 230.

As will of course be understood, graft stents suitable for use in treating diseased bifurcated lumens may be constructed using any of the processes described hereinabove. In particular, the graft material may either include a longitudinal seam, a flap of excess material, as described with respect to the embodiment of FIG. 11A, or a tube, as described for the embodiment of FIG. 12.

While preferred illustrative embodiments of the invention are described above, it will be apparent to one skilled in the art that various changes and modifications may be made therein without departing from the invention and it is intended in the appended claims to cover all such changes and modifications which fall within the true spirit and scope of the invention.

What is claimed is:

1. A method of making a graft stent for treating a section of a body lumen, the method comprising:

providing a coiled sheet of a resilient material, the coiled sheet having a surface, a contracted state of reduced diameter and an expanded state of enlarged diameter, the coiled sheet forming a series of overlapping turns in the contracted state; and affixing a biocompatible graft material to a portion of the surface of the coiled sheet, the graft material being wound within the overlapping turns of the coiled sheet when the coiled sheet is wound to its contracted state.

2. The method as defined in claim 1 wherein affixing a biocompatible graft material to the surface of the coiled sheet comprises:

coating the surface of the coiled sheet with a biocompatible adhesive having a cured state, the biocompatible adhesive being flexible in the cured state; and adhering the coiled sheet to the biocompatible graft material.

3. The method as defined in claim 1 wherein providing a coiled sheet further comprises providing a coiled sheet having a plurality of teeth on one edge and mating openings that interengage the teeth on an opposing edge.

4. The method as defined in claim 1 further comprising:

trimming excess graft material from the coiled sheet to complete assembly of the graft stent; and sterilizing the graft stent.

5. The method as defined in claim 1 wherein affixing a biocompatible graft material to the surface of the coiled sheet comprises suturing or stitching the biocompatible graft material to the coiled sheet.

6. The method as defined in claim 1 wherein affixing a biocompatible graft material to the surface of the coiled sheet comprises dipping the coiled sheet into a curable biocompatible liquid polymer, the biocompatible liquid polymer forming the biocompatible graft material when cured.

7. A method for making a graft stent for treating a section of a body lumen, the method comprising:

providing a sheet including a lattice and a surface, the sheet having an initial flat shape and being capable of being formed into a coiled shape;

forming the sheet into the coiled shape, the coiled shape having a series of overlapping turns; and affixing a biocompatible graft material to at least a portion of the surface of the sheet, the biocompatible graft material being wound within the overlapping turns when the sheet is in the coiled shape.

8. The method as defined in claim 7, wherein the affixing step comprises:

coating at least a portion of the surface of the sheet with a biocompatible adhesive; and bonding the sheet to the biocompatible graft material with the biocompatible adhesive.

9. The method as defined in claim 7, wherein the affixing step comprises suturing the sheet and biocompatible graft material together.

10. The method as defined in claim 7, wherein the affixing step comprises:

dipping the sheet into a liquid polymer; and bonding the sheet to the biocompatible graft material with the liquid polymer.

11. The method as defined in claim 7, wherein the affixing step comprises:

dipping the sheet into a liquid polymer to form a film along the surface of the sheet; and curing the liquid polymer, the cured polymer film comprising the biocompatible graft material.

12. The method as defined in claim 11, wherein the lattice comprises a multiplicity of openings therein, and wherein the film extends across the multiplicity of openings when the sheet is dipped therein.

13. The method as defined in claim 7, wherein the winding step comprises spirally winding the sheet into the coiled shape to provide an outer overlapping edge that spirals around an outer surface of the sheet.

14. The method as defined in claim 7, wherein a length of the biocompatible graft material is left extending from an edge of the sheet to form a flap when the biocompatible graft material is affixed to the sheet, and wherein the flap is wound to overlap a longitudinal seam extending along an outer surface of the sheet when the sheet is formed into the coiled shape.

15. The method as defined in claim 7, further comprising affixing a tubular graft to an opening in the surface of the sheet.

16. The method as defined in claim 15, further comprising providing a suture loop through an end of the tubular graft.

17. The method as defined in claim 7, wherein the sheet comprises first and second sheets, and wherein the affixing step comprises sandwiching the biocompatible graft material between the first and second sheets.

18. The method as defined in claim 17, wherein the first and second sheets are glued together with an adhesive, trapping the biocompatible graft material therebetween.

19. The method as defined in claim 17, wherein the first and second sheets comprise mating projections and sockets, and wherein the affixing step comprises inserting the projections into the mating sockets.

20. A method for making a graft stent for treating a section of a body lumen, the method comprising:

providing a sheet including a surface, the sheet having an initial flat shape and being capable of being formed into a coiled shape;

forming the sheet into the coiled shape having a series of overlapping turns;

providing a pair of layers of biocompatible graft material; and affixing the sheet between the pair of layers of biocompatible graft material, at least a portion of one of the layers of biocompatible graft material being wound within the overlapping turns when the sheet is in the coiled shape.

21. The method as defined in claim 20, wherein the sheet comprises a multiplicity of openings, and wherein the affixing step comprises:

sandwiching the sheet between the two layers of biocompatible graft material; and heating the biocompatible graft material to a temperature at which the two layers fuse together through the multiplicity of openings.

22. The method as defined in claim 21, wherein the affixing step further comprises applying pressure to the pair of layers of biocompatible graft material during the heating step.

23. The method as defined in claim 21, wherein the affixing step further comprises suturing the pair of layers of biocompatible graft material to the sheet.

24. The method as defined in claim 20, wherein the affixing step comprises:

affixing the pair of layers of biocompatible graft material together;

inserting the sheet between the affixed pair of layers of biocompatible graft material; and stitching the sheet to the affixed pair of layers of biocompatible graft material.

25. The method as defined in claim 24, wherein the step of affixing the pair of layers of biocompatible graft material together comprises sewing the pair of layers of biocompatible graft material together to form a pillow case structure into which the sheet is inserted.

* * * * *